(12) United States Patent
Maurin et al.

(10) Patent No.: US 6,399,605 B1
(45) Date of Patent: Jun. 4, 2002

(54) OPHTHALMIC COMPOSITION COMPRISING A BETA -BLOCKER

(75) Inventors: Florence Maurin, Vailhauques; Elisabeth Latour, Montpellier; Claude Coquelet, Perols, all of (FR)

(73) Assignee: Laboratoire Chauvin S.A., Montpellier Cedex (FR)

( * ) Notice: Subject to any disclaimer, the term of this patent is extended or adjusted under 35 U.S.C. 154(b) by 0 days.

(21) Appl. No.: 09/647,987

(22) PCT Filed: Mar. 17, 1999

(86) PCT No.: PCT/FR99/00612

§ 371 (c)(1),
(2), (4) Date: Dec. 28, 2000

(87) PCT Pub. No.: WO99/52559

PCT Pub. Date: Oct. 21, 1999

(30) Foreign Application Priority Data

Apr. 9, 1998 (FR) .............................................. 98 04489

(51) Int. Cl.⁷ ............................................ A61K 31/535
(52) U.S. Cl. ..................................... 514/236.2; 514/912
(58) Field of Search ............................... 514/236.2, 912

(56) References Cited

U.S. PATENT DOCUMENTS 5,318,780 A    6/1994    Viegas et al.

FOREIGN PATENT DOCUMENTS

| WO | WO 95/05803 | 3/1995 |
| WO | WO 95/35073 | 12/1995 |
| WO | WO 98/11874 | 3/1998 |

OTHER PUBLICATIONS

L.K. Ghosh, P. Sairman, P.K. Sharma, B.K. Gupta, "Development and Evaluation of an Oral Controlled Release Multiple Emulsion Drug Delivery System of a Specific Beta Blocker Metoprolol Tartrate", XP–002089212, Sep. 8, 1996.

*Primary Examiner*—Zohreh Fay
(74) *Attorney, Agent, or Firm*—Young & Thompson

(57) ABSTRACT

The invention concerns an ophthalmic composition comprising a beta-blocker solution, said composition being obtained by dissolving in water beta-blocker in the presence of alginic acid and adding an alkaline base, to obtain a solution with the PH of 6 to 8. Said composition has a sustained duration of action.

9 Claims, No Drawings

OPHTHALMIC COMPOSITION COMPRISING A BETA-BLOCKER

The present invention relates to ophthalmic compositions comprising a β-blocker.

Ophthalmic compositions comprising β-blockers are used in the treatment of ocular hypertension and of glaucoma. As examples, there may be mentioned collyria based on carteolol, timolol, befunolol, metipranolol, levobunolol, pindolol or betaxolol. These solutions have a relatively short duration of action, such that the administration of these collyria should be repeated during the day.

Cohen et al. (Journal of Control Release, 44, 201, 1997) have moreover proposed aqueous solutions of pilocarpine containing a sodium alginate with a high guluronic acid content, which form a gel when the solution is applied to the eye (apparently because of the action of the calcium ions present in the lachrymal fluid) and make it possible to obtain a prolonged duration of action.

The inventors have however observed that if this system is applied to β-blockers, that is to say if a β-blocker is added to a sodium alginate solution, no prolonged effect is obtained after administration of the solution.

The inventors have on the other hand discovered that if a β-blocker is added to an aqueous composition containing alginic acid and the pH is increased by addition of an alkaline base, a solution is obtained which makes it possible to obtain a prolonged effect after administration and which thereby allows a single daily administration.

The subject of the present invention is thus an ophthalmic composition comprising a β-blocker in solution, this composition being obtained by dissolving the β-blocker in water in the presence of alginic acid and adding an alkaline base, in order to obtain a solution having a pH of 6 to 8.

The subject of the present invention is also a method of preparing an ophthalmic composition, consisting in dissolving a β-blocker in water in the presence of alginic acid and in adding an alkaline base in order to bring its pH to a value of 6 to 8.

The alginic acid is preferably an alginic acid having a guluronic acid content of at least 40% and, preferably, of at least 65%, for example an alginic acid having a guluronic acid content of 65 to 75%.

The β-blockers present in the composition may be chosen in particular from carteolol, timolol, befunolol, metipranolol, levobunolol, pindolol or betaxolol.

The β-blockers are added in general in the form of salts with pharmaceutically acceptable acids.

They are generally present at concentrations of 0.01 to 5% and preferably of 0.1 to 2% (expressed in the form of a base) of the weight of the final composition.

The alginic acid is used at concentrations of 0.01 to 5% and, preferably, between 0.1 and 2% of the weight of the final composition.

The alginic acid/β-blocker (expressed in the form of a base) weight ratio is in general from 0.1 to 20 and preferably from 0.2 to 10.

The alkaline base is an alkali metal hydroxide or a basic salt of an alkali metal and is preferably sodium hydroxide.

The composition may in addition contain a buffer mixture such as a phosphate buffer, an isotonizing agent such as sodium chloride, stabilizers such as an antioxidant and/or a chelating agent (for example EDTA), as well as a preservative such as benzalkonium chloride.

Results of trials demonstrating the effects obtained with the compositions according to the invention will be given below.

1) COMPARATIVE TRIALS WITH CARTEOLOL

The procedures used were the following:

Procedure 1

Alginic acid is suspended in about 50 ml of purified water and carteolol hydrochloride (2 g) is dissolved therein. The pH is then close to 3.

The phosphate buffer (0.1 g of sodium hydrogen phosphate dodecahydrate and 0.04 g of sodium dihydrogen phosphate dihydrate) is added followed by sodium chloride. The pH then reaches a value close to 3.5.

The pH is adjusted to 6.8 with a 1 N sodium hydroxide solution and benzalkonium chloride (0.005 g) is incorporated therein.

The volume is finally adjusted to 100 ml by addition of purified water.

Procedure 2

Sodium alginate is dissolved in about 50 ml of purified water, the value of the pH is close to 8.

Carteolol hydrochloride (2 g), phosphate buffer and sodium chloride are dissolved in 40 ml of purified water (the pH of the solution is close to 6.8).

This solution is added to the aqueous solution of sodium alginate and the pH adjusted to 6.8 by addition of dilute hydrochloric acid.

Benzalkonium chloride (0.005 g) is incorporated therein and the final volume is adjusted to 100 ml by addition of purified water.

Procedure 3

Alginic acid is suspended in about 50 ml of purified water and then the pH is adjusted to 8 by addition of a 1 N sodium hydroxide solution.

Carteolol hydrochloride (2 g), phosphate buffer and sodium chloride are dissolved in 40 ml of purified water (the pH of the solution is close to 6.8).

This latter solution is added to the neutralized alginic acid solution and the pH is adjusted to 6.8 by addition of dilute hydrochloric acid.

Benzalkonium chloride (0.005 g) is incorporated therein and the final volume is adjusted to 100 ml by addition of purified water.

These compositions were tested in a model of ocular hypertension triggered in rabbits.

Animals

The experiments were performed on New Zealand male albino rabbits obtained from the Charles River Breeding Farm, France (St Aubin les Elbeuf, 76140 Cléon) acclimatized for a minimum of five days in the animal house (temperature: 19±2° C., relative humidity: 55±10%, illumination: 12 hours of daylight—12 hours of darkness).

Ocular Hypertension Triggered by Aqueous Fluid Overload

The animals were starved of food on the day before the experiments. On the day of the experiment, the animals were conditioned to stalling in a restraining cage and to the measurement of intraocular pressure (IOP) until a stable base value is obtained. The IOP was measured with the aid of an ALCON aplanation pneumatonograph or a MENTOR® pneumatonometer (model 30 Classic), without preliminary local anaesthesia.

The ophthalmic preparations tested were then administered in one eye, in a volume of 25 µl, at various times before the aqueous fluid overload: the contralateral eye received no treatment and served as a control.

The experimental ocular hypertension was induced in the two eyes by oral administration of water at 37° C. (70 ml/kg in less than 30 seconds; 200 ml for the rabbits having a weight greater than 3 kg). The IOP was measured in the two eyes before, and then every ten minutes for one hour after the aqueous fluid overload.

The ocular hypotensive activity of the preparations tested is calculated from the increases in IOP in the treated eye and the control eye, at the experimental hypertension peak; it is expressed as a percentage of inhibition of the hypertension (mean±standard deviation).

Estimation of the Maximum Activity and of the Duration of Action of the Preparations Tested The ocular hypertension triggered by an aqueous fluid overload is an acute hypertension since the IOP returns to its base value on average one hour after the aqueous fluid overload. The hypotensive activity peak and the duration of action of the preparations tested cannot therefore be evaluated in a single experiment; a fairly precise estimation of these two parameters is obtained indirectly on several experiments by varying the time of administration of the preparations in relation to the aqueous fluid overload (pretreatment time).

The results are assembled in the table below.

TABLE

Ocular hypotensive activity expressed as % inhibition of the hypertension induced by an aqueous fluid overload in rabbits

| Composition | Alginic derivative | Pretreatment time | | |
|---|---|---|---|---|
| | | 1 h | 6 h | 8 h |
| 1 | — | 25.5 ± 6.2 (13) ** | 15.2 ± 8.2 (8) | 0.6 ± 5.6 (4) |
| 2 (1) * | Alginic acid 1% (G = between 65 and 75%) | 24.4 ± 4.8 (5) | 13.2 ± 6.0 (5) | 10.0 ± 6.1 (4) |
| 3 (1) | Alginic acid 1% (G = 39%) | | 12.5 ± 2.1 (4) | 3.6 ± 4.0 (5) |
| 4 (2) | Sodium alginate 1% LVG (G = between 65 and 75%) | | | 1.9 ± 1.5 (4) |
| 5 (2) | Sodium alginate 1% MVG (G = between 65 and 75%) | | | −0.2 ± 1.6 (4) |
| 6 (3) | Sodium alginate formed in situ from alginic acid 1% (G = between 65 and 75%) | | | 1.6 ± 3.5 (5) |

* ( ) procedure
** ( ) number of animals
G: guluronic acid content
LVG: low viscosity; MVG = medium viscosity.

An ophthalmic solution based on 2% carteolol hydrochloride with no alginic derivative (composition 1) no longer has any activity after 8h00 of pretreatment.

A corresponding ophthalmic composition according to the invention (composition 2) containing 1% alginic acid (alginic acid containing between 65 and 75% of guluronic acid) still has at time 8h00 a significant inhibition of the ocular hypertension.

The use of alginic acid at the concentration of 1% whose guluronic acid content is 39% leads to a carteolol hydrochloride composition at 2% (composition 3) inducing a lower reduction in the ocular hypertension at time 8h00 than a composition containing 1% of alginic acid whose guluronic acid content is higher, between 65 and 75%.

The use of sodium alginate at the concentration of 1% whose guluronic acid content is between 65 and 75% does not make it possible to obtain ophthalmic compositions based on 2% carteolol hydrochloride exhibiting inhibition of the ocular hypertension after 8h00 of pretreatment. These results are observed with sodium alginate of low viscosity and of medium viscosity (compositions 4 and 5).

If, during the preparation of the ophthalmic composition, the alginic acid (at the concentration of 1%) is salified by addition of sodium hydroxide to pH 8 before the addition of carteolol hydrochloride, no inhibition of the ocular hypertension induced is observed after 8h00 of pretreatment (composition 6). The formation of alginate in situ from alginic acid with a guluronic acid content of between 65 and 75% does not make it possible to obtain the pharmacological effect observed with composition 2.

2) Trials with β-blockers Other than Carteolol
a) Timolol

A study of the ocular hypotensive activity as a function of the alginic acid concentration (% expressed by weight relative to the weight of the final composition) was carried out on timolol at the concentration of 0.5% (expressed as a base; that is 0.683% of timolol maleate) in preparations according to procedure 1 using an alginic acid with a high guluronic acid content (G greater than 65%):

Ocular Hypotensive Activity Expressed as % Inhibition of the Hypertension Induced by an Aqueous Fluid Overload in Rabbits

| Alginic acid (as % of the weight of the final composition) | Pretreatment time | |
|---|---|---|
| | 6 h | 8 h |
| 0* | 13.2 ± 4.3 (4) | 1.5 ± 4.4 (6) |
| 0.16 | | 8.5 ± 2.7 (4) |
| 0.32 | | 7.6 ± 4.2 (4) |
| 0.64 | | 8.2 ± 4.0 (5) |

*commercial collyrium containing 0.5% of timolol expressed as a base.

The commercial reference collyrium no longer has any activity after 8h00 of pretreatment. On the other hand, the effect is prolonged when the composition contains alginic acid.

b) Pindolol

A similar study was carried out with pindolol, used in the form of a base, at the concentration of 1%.

| Alginic acid (as % of the weight of the final composition) | Pretreatment time | |
|---|---|---|
| | 1 h | 4 h |
| 0* | 13.0 ± 6.6 (4) | −3.0 ± 8.7 (7) |
| 0.8 | | 10.3 ± 4.4 (4) |
| 1.6 | | 6.8 ± 1.7 (4) |

*commercial collyrium containing 1% of pindolol.

The commercial collyrium no longer has any activity after 4h00 of pretreatment.

The addition of alginic acid makes it possible to increase the duration of action of 1% pindolol.

3) Additional Trials on Carteolol

The ocular hypotensive activity of carteolol as a function of the alginic acid concentration was studied for various concentrations of carteolol hydrochloride: 0.5%–1% and 2% (that is respectively 0.44%–0.89% and 1.78% expressed in the form of a base).

The results are given in the following three tables, in comparison with commercial collyria without alginic acid and containing 0.5%–1% and 2% of carteolol hydrochloride.

0.5% carteolol hydrochloride

| Alginic acid (as % of the weight of the final composition) | Pretreatment time | |
| --- | --- | --- |
| | 4 h | 6 h |
| 0 | 11.4 ± 4.3 (4) | 1.3 ± 1.7 (4) |
| 0.25 | | 8.8 ± 4.7 (5) |
| 1 | | 5.9 ± 3.1 (5) |

1% carteolol hydrochloride

| Alginic acid (as % of the weight of the final composition) | Pretreatment time | |
| --- | --- | --- |
| | 6 h | 6 h |
| 0 | 10.6 ± 3.9 (4) | −0.2 ± 2.8 (5) |
| 0.5 | | 6.3 ± 2.8 (4) |
| 1 | | 10.1 ± 3.8 (4) |

2% carteolol hydrochloride

| Alginic acid (as % of the weight of the final composition) | Pretreatment time | |
| --- | --- | --- |
| | 6 h | 8 h |
| 0 | 15.2 ± 8.2 (8) | 0.6 ± 5.6 (4) |
| 1 | | 8.0 ± 2.7 (4) |
| 2 | | 11.4 ± 2.2 (5) |

What is claimed is:

1. Ophthalmic composition comprising a β-blocker in solution, this composition being obtained by dissolving the β-blocker in an aqueous alginic acid solution and then adding an alkaline base, in order to obtain a solution having a pH of 6 to 8.

2. Composition according to claim 1, in which the alginic acid has a guluronic acid content of at least 40%.

3. Composition according to claim 2, in which the alginic acid has a guluronic acid content of at least 65%.

4. Composition according to claim 1, in which the β-blocker is chosen from carteolol, timolol and pindolol.

5. Composition according to claim 1, in which the β-blocker is present at a concentration of 0.01 to 5% by weight.

6. Composition according to claim 1, in which the alginic acid is present at a concentration of 0.01 to 5% by weight.

7. Composition according to claim 1, in which the alginic acid/β-blocker weight ratio is from 0.1 to 20.

8. Composition according to claim 7, in which the alginic acid/β-blocker weight ratio is from 0.2 to 10.

9. Method of preparing an ophthalmic composition, comprising dissolving a β-blocker in an aqueous alginic acid solution and then adding an alkaline base in order to bring its pH to a value of 6 to 8.

* * * * *